(12) United States Patent
Wang et al.

(10) Patent No.: US 11,772,076 B2
(45) Date of Patent: Oct. 3, 2023

(54) PREPARATION METHOD OF NITROGEN-DOPED HIERARCHICAL-POROUS CARBON-LOADED NANOMETER PD CATALYST AND PRODUCT AND APPLICATION THEREOF

(71) Applicant: ZHEJIANG UNIVERSITY, Zhejiang (CN)

(72) Inventors: Yong Wang, Hangzhou (CN); Shanjun Mao, Hangzhou (CN); Zhe Wang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 235 days.

(21) Appl. No.: 17/074,548

(22) Filed: Oct. 19, 2020

(65) Prior Publication Data

US 2021/0121855 A1 Apr. 29, 2021

(30) Foreign Application Priority Data

Oct. 28, 2019 (CN) .......................... 201911028624.3

(51) Int. Cl.
*B01J 21/18* (2006.01)
*B01J 23/44* (2006.01)
(Continued)

(52) U.S. Cl.
CPC ............... *B01J 23/44* (2013.01); *B01J 21/18* (2013.01); *B01J 35/002* (2013.01); *B01J 35/023* (2013.01);
(Continued)

(58) Field of Classification Search
CPC . B01J 21/18; B01J 23/44; B01J 35/002; B01J 35/023; B01J 37/00; B01J 37/035;
(Continued)

(56) References Cited

U.S. PATENT DOCUMENTS

| 5,543,378 A * | 8/1996 | Wang ...................... B01J 23/44 |
| | | 423/445 B |
| 8,227,640 B2 * | 7/2012 | Ying ...................... C07B 37/04 |
| | | 564/473 |

(Continued)

FOREIGN PATENT DOCUMENTS

CN 102513099 A 6/2012

*Primary Examiner* — Cam N. Nguyen
(74) *Attorney, Agent, or Firm* — Maschoff Brennan (57) ABSTRACT

Disclosed are a nitrogen-doped hierarchical-porous carbon-loaded nano-Pd catalyst and a preparation method thereof. The preparation method includes preparing nitrogen-doped hierarchical-porous carbon, mixing the nitrogen-doped hierarchical-porous carbon with water, adjusting a pH value of the mixed solution to be alkaline, mixing the mixed solution with a Pd metal precursor aqueous solution, and then adding a reducing agent to obtain the nitrogen-doped hierarchical-porous carbon-loaded nano-Pd catalyst after reduction. The prepared nitrogen-doped hierarchical-porous carbon-loaded nano-Pd catalyst includes a nitrogen-doped porous carbon material carrier with hierarchical pores and Pd metal nanoparticles loaded in the hierarchical pores of the carrier. The Pd metal nanoparticles have a size of 2~14 nm and a regular polyhedron shape. The nitrogen-doped hierarchical-porous carbon-loaded nano-Pd catalyst has excellent catalytic performance, especially has ultra-high conversion rate, selectivity and cycle stability in the selective hydrogenation reaction of unsaturated ketones, and is a key to open a new synthetic route of vitamin E.

20 Claims, 9 Drawing Sheets

(51) Int. Cl.
  *B01J 35/00* (2006.01)
  *B01J 35/02* (2006.01)
  *B01J 37/00* (2006.01)
  *B01J 37/03* (2006.01)
  *B01J 3/04* (2006.01)
  *C07C 45/00* (2006.01)
  *C07C 47/02* (2006.01)

(52) U.S. Cl.
  CPC ............ *C07C 45/002* (2013.01); *C07C 47/02* (2013.01); *C07C 2521/18* (2013.01); *C07C 2523/44* (2013.01)

(58) Field of Classification Search
  CPC ........ B01J 37/04; C07C 45/002; C07C 45/02; C07C 47/02
  USPC .......................................... 502/182–185, 339
  See application file for complete search history.

(56) References Cited

U.S. PATENT DOCUMENTS

| | | | | |
|---|---|---|---|---|
| 10,195,587 | B2* | 2/2019 | Bakker | B01J 23/44 |
| 10,737,250 | B2* | 8/2020 | Wang | C07C 403/08 |
| 10,875,015 | B2* | 12/2020 | Zhou | B01J 35/04 |
| 11,325,112 | B2* | 5/2022 | Matsui | B01J 31/28 |
| 11,331,725 | B2* | 5/2022 | Chen | B01J 35/0013 |
| 11,339,482 | B2* | 5/2022 | Sugano | B01J 23/38 |
| 2018/0345265 | A1* | 12/2018 | Wang | B01J 23/20 |

\* cited by examiner

PREPARATION METHOD OF NITROGEN-DOPED HIERARCHICAL-POROUS CARBON-LOADED NANOMETER PD CATALYST AND PRODUCT AND APPLICATION THEREOF

TECHNICAL FIELD

The present invention relates to the technical field of catalysts, in particular to a preparation method of a nitrogen-doped hierarchical-porous carbon-loaded nanometer Pd catalyst and a product and an application thereof.

BACKGROUND ART

The selective hydrogenation reaction of unsaturated ketones is one of the key reactions in the production of vitamins, flavors, spices and other fine chemicals. Especially, the yield and cost of this selective hydrogenation reaction determine the economy of a new route of vitamin E synthesis. At present, catalysts used for the selective hydrogenation reaction of carbon-carbon double bonds of unsaturated ketones in industrial production are mainly loaded palladium (Pd) catalysts, such as commonly used palladium (Pd)/activated carbon (AC) catalysts. However, traditional Pd/AC catalysts have many problems such as low activity, serious loss of active components, insufficient selectivity, and over hydrogenation. Therefore, there is an urgent need to develop a more efficient and stable catalyst for the selective hydrogenation reaction of carbon-carbon double bonds of unsaturated ketones.

A carbon material has a large specific surface area and is easy to control, thereby being an ideal catalyst carrier. However, the traditional activated carbon surface is inert, and less interacted with a loaded metal, which easily causes the agglomeration and loss of active metal. In order to improve the performances of the carbon material, the Chinese patent document (Application No: CN 102513099 A) discloses a novel mesoporous carbon-loaded metal catalyst, which consists of metal particles and a mesoporous carbon carrier, the mesoporous carbon carrier being made of a heteroatom-doped mesoporous carbon material. In this technical solution, nitrogen doping is used to change a local electronic structure of the carbon material, thereby achieving the dispersion of noble metal nanoparticles, and improving the activity and stability of the catalyst through the interaction between nitrogen and metal. However, a nitrogen-doped carbon-loaded noble metal catalyst prepared by the traditional noble metal-loading method cannot solve the problems of insufficient selectivity and over hydrogenation during the selective hydrogenation reaction of carbon-carbon double bonds of unsaturated ketones. The reason resides in that the metal nanoparticles prepared by the traditional noble metal-loading method are spherical, with too many exposed corners, which is beneficial to the adsorption and hydrogenation of polar carbon-oxygen double bonds in the unsaturated ketones, resulting in a decrease in selectivity.

Therefore, how to simply and controllably load Pd nanoparticles with a minimum proportion of corner atoms on nitrogen-doped carbon so as to further improve the selectivity of a catalyst is a difficult problem for the preparation of this type of catalyst.

SUMMARY OF THE INVENTION

In view of the above-mentioned problems in the prior art, the present invention discloses a preparation method of a nitrogen-doped hierarchical-porous carbon-loaded nanometer Pd catalyst. Metal Pd nanoparticles with a regular morphology of polyhedron and a particle size of about 2-14 nm are loaded on the surface of nitrogen-doped hierarchical-porous carbon and in hierarchical-pores. The metal Pd nanoparticles with specific morphology and particle size have relatively few corner atoms, such that the prepared nitrogen-doped hierarchical-porous carbon-loaded nano-Pd catalyst has excellent catalytic performance, especially has ultra-high conversion rate, selectivity and cycle stability in the selective hydrogenation reaction of unsaturated ketones.

The specific technical solution are as follows:

A preparation method of a nitrogen-doped hierarchical-porous carbon-loaded nano-Pd catalyst, comprising:

1) preparing nitrogen-doped hierarchical-porous carbon;
2) mixing the nitrogen-doped hierarchical-porous carbon prepared in step 1) with water, and adjusting a pH value of the mixed solution to be alkaline; and
3) mixing the mixed solution prepared in step 2) with a Pd metal precursor aqueous solution, and then adding a reducing agent to obtain the nitrogen-doped hierarchical-porous carbon-loaded nano-Pd catalyst after reduction.

In the preparation method of the present invention, nitrogen-doped hierarchical-porous carbon is used as a carrier, a pH value of a mixed solution composed of the nitrogen-doped hierarchical-porous carbon and water is adjusted to be alkaline prior to adding a Pd metal precursor, such that the Pd metal precursor is first converted into Pd hydroxide under alkaline conditions and nucleates uniformly in the solution. Pd hydroxide nanoparticles with regular shapes and uniform sizes are then formed, and attached into hierarchical-pores of the nitrogen-doped hierarchical-porous carbon and combined with nitrogen species contained therein. The size and morphology of the Pd hydroxide nanoparticles can be controlled and adjusted in accordance with the type and concentration of the Pd metal precursor and the pH value of the mixed solution prepared in step 2). Finally, the Pd hydroxide nanoparticles are converted into Pd metal nanoparticles after being reduced by a reducing agent. During the reduction process, the type and concentration of the reducing agent will also affect the particle size of the converted Pd metal nanoparticles.

The nitrogen-doped hierarchical-porous carbon is selected as the carrier, so that the Pd hydroxide nanoparticles formed in the solution can be uniformly dispersed in the pores of the hierarchical-porous carbon by interacting with nitrogen species. In addition, the Pd metal nanoparticles formed by the reduction of the Pd hydroxide nanoparticles can also be stabilized by the nitrogen species, and are not easy to agglomerate and lose, thereby ensuring the stability of the prepared catalyst during the using process. In addition, due to large sizes of the Pd metal nanoparticles, the Pd metal nanoparticles can be prevented from clogging the pores by nitrogen-doped hierarchical-porous carbon, thereby improving a mass transfer effect.

In the reduction process, a low-temperature liquid phase reduction method is used to make good use of a shape-preserving effect of the Pd hydroxide nanoparticles, so as to avoid the destruction of high-temperature hydrogen reduction on the Pd hydroxide nanoparticles, thereby reducing the number of corners on the surfaces of the Pd metal nanoparticles as much as possible. This shape-preserving effect gives the prepared catalyst excellent hydrogenation selectivity.

Through comparative experiments, it is found that the traditional impregnation method is used to first mix the carrier with the Pd metal precursor, then adjust the mixed solution to be alkaline, and finally add the reducing agent. In the loaded catalyst prepared by the traditional process, the metal Pd nanoparticles are spherical or ellipsoidal. After further testing, it is found that the conversion rate and selectivity of the catalyst prepared by the traditional process in the selective hydrogenation reaction of unsaturated ketones are much lower than those of the catalyst prepared in the present invention.

In step 1), the preparation of the nitrogen-doped hierarchical-porous carbon refers to a method in the patent (Application No: CN 106179440 A).

The prepared nitrogen-doped hierarchical-porous carbon has a hierarchical-porous structure, and the nitrogen species contained therein can be used to stabilize the metal Pd nanoparticles. In the nitrogen-doped hierarchical-porous carbon, a mass fraction of nitrogen element is 0.5~15%.

In step 2):
the nitrogen-doped hierarchical-porous carbon is insoluble in water, and a mixed solution formed after mixing with water is a suspension. Preferably, a mass-volume ratio of the nitrogen-doped hierarchical-porous carbon to water is 1:20~200 g/mL.

In step 2), the pH value of the mixed solution is adjusted to be alkaline, preferably to 8~12, thereby ensuring that the particle size and morphology of the Pd hydroxide nanoparticles are adjusted under the conditions for forming the Pd hydroxide, so as to maintain the shape and size of the Pd metal nanoparticles in the subsequent reduction step.

In step 3):
the Pd metal precursor is selected from soluble salts of Pd metal, and specifically may be selected from at least one of $PdCl_2$, $H_2PdCl_4$, $Pd(NO_3)_2$ and $Pd(NH_3)_4(NO_3)_2$.

In the preparation method of the present invention, the size and morphology of the Pd hydroxide nanoparticles as an intermediate may be adjusted by adjusting the type of the Pd metal precursor, the concentration of the Pd metal precursor aqueous solution, and the pH value of the mixed solution. Preferably, the concentration of the Pd metal precursor aqueous solution is 1~50 mg/mL, and a mass ratio of the nitrogen-doped hierarchical-porous carbon to the Pd metal precursor is (3~600):1.

The particle size of the Pd hydroxide nanoparticles prepared under the above process parameters is 3~15 nm, preferably 4~10 nm.

The mixing of the mixed solution and the Pd metal precursor aqueous solution is carried out under continuous stirring conditions.

In step 3):
the reducing agent is selected from at least one of hydrazine hydrate, formic acid, sodium borohydride, and sodium formate; and
a mass ratio of the reducing agent to the Pd metal precursor is (1~20):1.

The reducing agent is added in a form of a reducing agent aqueous solution, and continuously stirred for 0.1~10 hours during the dropping process of the reducing agent. Preferably, the mass-volume ratio of the reducing agent to water is 1~20 mg/mL.

The reduction temperature is 0~80° C., and the reduction time is 1~360 min. The preferred temperature is 0~30° C.

By changing the type and concentration of the reducing agent, the particle size of the Pd metal nanoparticles obtained after reduction can be adjusted.

The reduced product also needs to be filtered to obtain the nitrogen-doped hierarchical-porous carbon-loaded nano-Pd catalyst.

In addition, in order to prevent the catalyst from igniting spontaneously in the air, the filtered nitrogen-doped hierarchical-porous carbon-loaded nano-Pd catalyst needs to contain a certain amount of moisture. Preferably, the water content of the nitrogen-doped hierarchical-porous carbon-loaded nano-Pd catalyst is 5~75 wt %.

The present invention also discloses a nitrogen-doped hierarchical-porous carbon-loaded nano-Pd catalyst prepared according to the above method, comprising a nitrogen-doped porous carbon material carrier with hierarchical pores, and Pd metal nanoparticles loaded on the carrier and located in the hierarchical pores of the carrier.

The Pd metal nano-particles have a particle size of 2~14 nm and a shape of a regular polyhedron, and the nitrogen species on the surface of the nitrogen-doped porous carbon material are stable. Preferably, the Pd metal nanoparticles have a particle size of 4~10 nm.

Based on the total mass of the dehydrated and dried catalyst, the mass fraction of the Pd metal nanoparticles is 0.1~10%.

The composition and morphology of the nitrogen-doped hierarchical-porous carbon-loaded nano-Pd catalyst directly depend on its preparation process conditions.

Further preferably, the preparation process of the nitrogen-doped hierarchical-porous carbon-loaded nano-Pd catalyst is as follows:

in step 2):
the pH value of the mixed solution is adjusted to 9~10;
in step 3):
the Pd metal precursor is selected from $PdCl_2$, $Pd(NO_3)_2$ or $Pd(NH_3)_4(NO_3)_2$; the concentration of the Pd metal precursor aqueous solution is 5~20 mg/mL; a mass ratio of the nitrogen-doped hierarchical-porous carbon to the Pd metal precursor is (50~200):1;
the reducing agent is selected from hydrazine hydrate, formic acid or a sodium borohydride aqueous solution with a concentration of 10~20 mg/mL; a mass ratio of the reducing agent to the Pd metal precursor is (2~6):1.

Further preferably:
the concentration of the Pd metal precursor aqueous solution is 10 mg/mL; a mass ratio of the nitrogen-doped hierarchical-porous carbon to the Pd metal precursor is 100:1; the concentration of the reducing agent is 10~20 mg/mL; the mass ratio of the reducing agent to the Pd metal precursor is (2~4):1.

In the nitrogen-doped hierarchical-porous carbon-loaded nano-Pd catalyst prepared under the above-mentioned optimized process conditions, the Pd metal nanoparticles present a regular polyhedral shape, with an average particle size of 4~8 nm, and conform to a normal distribution.

Still further preferably, the pH value of the mixed solution is 10, and the Pd metal precursor is selected from $PdCl_2$. In the nitrogen-doped hierarchical-porous carbon-loaded nano-Pd catalyst prepared under further preferred conditions, the Pd metal nanoparticles have an average particle size of 8 nm, and have better selectivity because the content of Pd metal nanoparticles with a particle size of less than 4 nm is extremely low.

The present invention also discloses an application of the nitrogen-doped hierarchical-porous carbon-loaded nano-Pd catalyst in a catalytic hydrogenation reaction, especially an application in a selective hydrogenation reaction of unsaturated ketones.

In the above application, the nitrogen-doped hierarchical-porous carbon-loaded nano-Pd catalyst has universal applicability. After testing, when the following unsaturated ketones are used as substrates, they all have excellent catalytic performances. The unsaturated ketones specifically include: 6-methyl-5-heptene-2-one, 6-methyl-3,5-heptadiene-2-one, 6,10-dimethyl-5-ene-2-undecanone, 6,10-dimethyl-5,9-diene-2-undecanone, 6,10-dimethyl-3,5-diene-2-undecanone, 6,10,14-trimethyl-5-ene-2-pentadecanone, 6,10,14-trimethyl-5,9,13-triene-2-pentadecanone, 6,10,14-trimethyl-3,5-diene-2-pentadecanone, cis-3,7-dimethyl-2,6-diene-octanal, and trans-3,7-dimethyl-2,6-diene-octanal.

Compared with the prior art, the present invention has the following advantages:

the present invention discloses the preparation method of the nitrogen-doped hierarchical-porous carbon-loaded nano-Pd catalyst. The catalyst is prepared by the process steps of using the nitrogen-doped hierarchical-porous carbon as a carrier, adjusting the pH value of the mixed solution of the nitrogen-doped hierarchical-porous carbon and water first and then adding the Pd metal precursor, in combination with a low-temperature liquid phase reduction method, and the Pd metal nanoparticles in the catalyst exhibit a regular polyhedral shape.

In the preparation process of the present invention, the average particle size of the Pd metal nanoparticles in the prepared catalyst is also adjusted by adjusting the pH value of the mixed solution prepared in step 2), the type and concentration of the Pd metal precursor in step 3), and the type and concentration of the reducing agent. Furthermore, the catalyst prepared by matching the appropriate pH value of the mixed solution, the type and concentration of the Pd metal precursor, and the type and concentration of the reducing agent has ultra-high conversion rate, selectivity and cycle stability in the selective hydrogenation reaction of the unsaturated ketones.

DETAILED DESCRIPTION

The technical solutions in the embodiments of the present invention will be described clearly and completely below. Obviously, the described embodiments are only a part of the embodiments of the present invention, rather than all of the embodiments. Based on the embodiments of the present invention, all other embodiments obtained by those of ordinary skill in the art without creative work shall fall within the protection scope of the present invention.

Example 1

4 g of cellulose, 12 g of sodium bicarbonate and 12 g of ammonium oxalate are weighed, mechanically mixed and transferred to a 30 mL crucible, and then calcined in a nitrogen furnace. The calcination step is as follows: heating up to 800° C. at 10° C./min; calcining at 800° C. for 1 h; and then naturally cooling to room temperature. The calcined product is ground and mixed with deionized water, and then filtered after standing for 24 hours. The precipitate is then washed to neutrality, and dried to obtain a nitrogen-doped hierarchical-porous carbon material for later use.

1 g of nitrogen-doped hierarchical-porous carbon material is weighed, added to 60 mL of deionized water, stirred at room temperature, and slowly added with 100 mg/mL NaOH aqueous solution dropwise to adjust the pH value of the mixed solution to 10. 1 mL of 10 mg/mL $PdCl_2$ aqueous solution is then added dropwise, and continuously stirred for 1 h at room temperature. 2 mL of 10 mg/mL formic acid aqueous solution is added dropwise under stirring conditions, continuously stirred at room temperature for 1 h, filtered and washed to neutrality, to obtain a nitrogen-doped hierarchical-porous carbon-loaded nano-Pd catalyst.

An actual load of Pd in the nitrogen-doped hierarchical-porous carbon-loaded nano-Pd catalyst prepared in this example is tested by using an atomic emission spectroscopy, to obtain a result of 0.59%, which is basically consistent with a theoretical load of the Pd.

Figure 1:
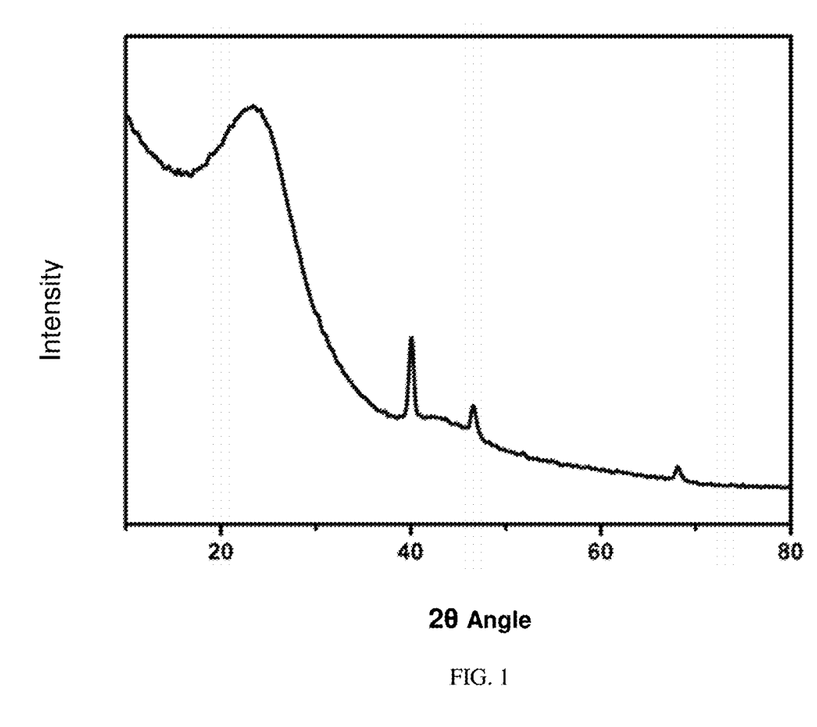
FIG. 1 is an X-ray diffraction diagram of a nitrogen-doped hierarchical-porous carbon-loaded nano-Pd catalyst prepared in Example 1.
Figure 2:
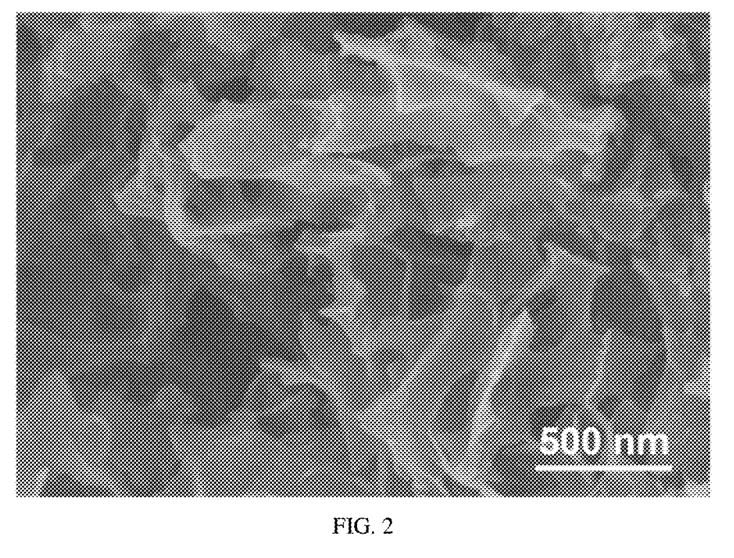
FIG. 2 is a scanning electron micrograph of the nitrogen-doped hierarchical-porous carbon-loaded nano-Pd catalyst prepared in Example 1.
Figure 3:
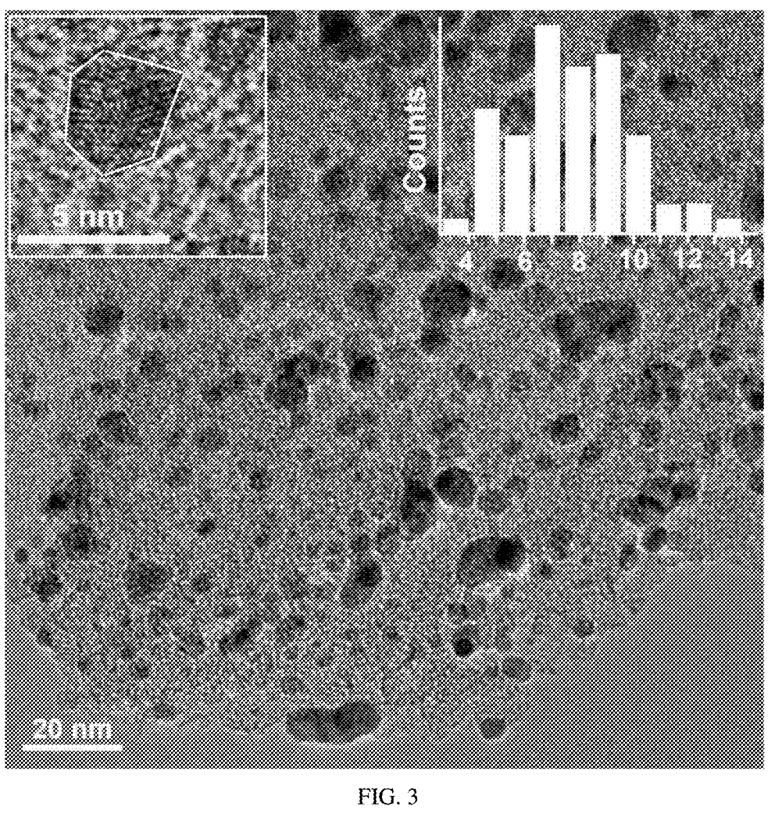
FIG. 3 is a transmission electron micrograph of the nitrogen-doped hierarchical-porous carbon-loaded nano-Pd catalyst prepared in Example 1, in which a further enlarged image of the catalyst and the particle size distribution are provided in small pictures respectively.
Figure 4:
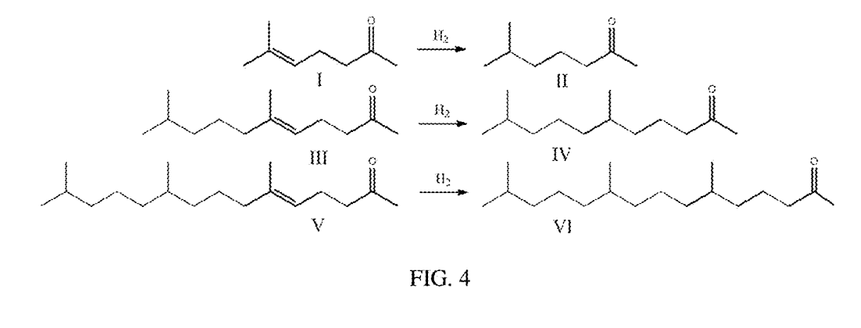
FIG. 4 is a chemical reaction formula of a selective hydrogenation reaction of monoketene on the nitrogen-doped hierarchical-porous carbon-loaded nano-Pd catalyst in the present invention.
Figure 5:
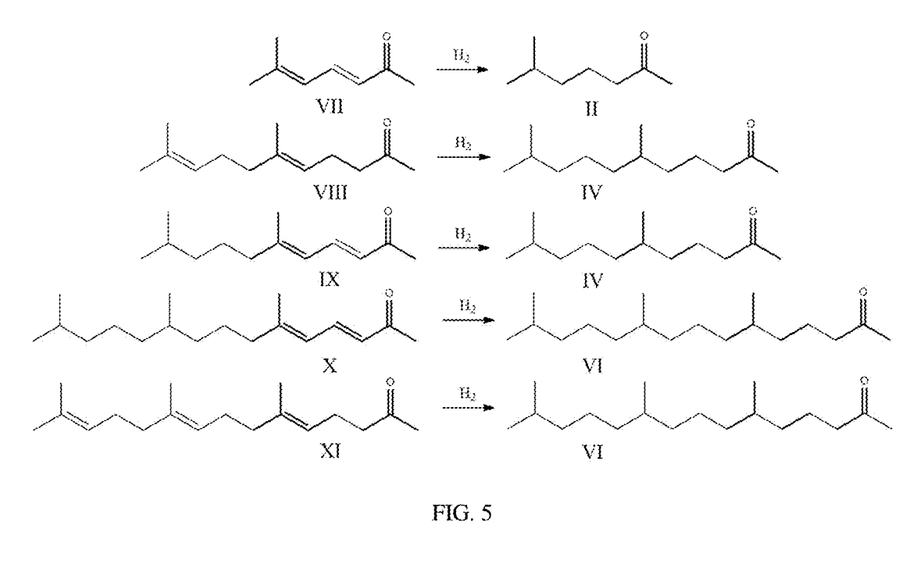
FIG. 5 is a chemical reaction formula of a selective hydrogenation reaction of diketene and triketene on the nitrogen-doped hierarchical-porous carbon-loaded nano-Pd catalyst in the present invention.
Figure 6:
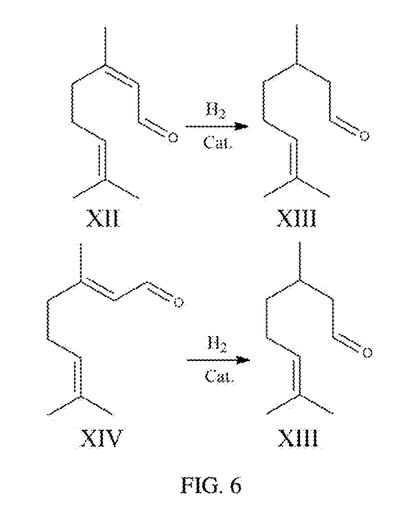
FIG. 6 is a chemical reaction formula of a selective hydrogenation reaction of diketene and triketene on the nitrogen-doped hierarchical-porous carbon-loaded nano-Pd catalyst in the present invention.

An X-ray diffraction test is performed on the nitrogen-doped porous carbon composite material prepared in this embodiment, and the results are shown in FIG. 1. As can be seen from FIG. 1, characteristic diffraction peaks of Pd metal can be clearly observed at 40.1° and 46.7°. A scanning electron microscopy test is performed on the nitrogen-doped hierarchical-porous carbon-loaded nano-Pd catalyst prepared in this example, and the results are shown in FIG. 2. As can be seen from FIG. 2, a rich pore structure can be clearly observed. A transmission electron microscope test is performed on the nitrogen-doped porous carbon composite material prepared in this example, and the results are shown in FIG. 3. As can be seen from FIG. 3, Pd nanoparticles are uniformly dispersed in the nitrogen-doped porous carbon material, and have a particle size conforming to a normal distribution. The average particle size of the Pd nanoparticles is about 8 nm, and the content of Pd nanoparticles with a particle size less than 4 nm is extremely low.

Example 2

1 g of nitrogen-doped hierarchical-porous carbon material prepared in Example 1 is weighed, added to 60 mL of deionized water, stirred at room temperature, and slowly added with 100 mg/mL NaOH aqueous solution dropwise to adjust the pH value of the mixed solution to 9. 1 mL of 10 mg/mL $Pd(NO_3)_2$ aqueous solution is then added dropwise, and continuously stirred for 1 h at room temperature. 2 mL of 15 mg/mL formic acid aqueous solution is added dropwise under stirring conditions, continuously stirred at room temperature for 1 h, filtered and washed to neutrality, to obtain a nitrogen-doped hierarchical-porous carbon-loaded nano-Pd catalyst.

In contrast to Example 1, the nitrogen-doped hierarchical-porous carbon-loaded nano-Pd catalyst prepared in this example is adjusted in the pH value of the mixed solution, the type of precursor salt, and the type and concentration of the reducing agent in the preparation process. The particle size of the Pd nanoparticles of the prepared catalyst conforms to the normal distribution, and the average particle size is about 6 nm, wherein the content of Pd nanoparticles with a particle size of less than 4 nm accounts for ~10%, which is more than that of Example 1.

Example 3

1 g of nitrogen-doped hierarchical-porous carbon material prepared in Example 1 is weighed, added to 60 mL of deionized water, stirred at room temperature, and slowly added with 100 mg/mL NaOH aqueous solution dropwise to adjust the pH value of the mixed solution to 10. 1 mL of 10 mg/mL $Pd(NH_3)_4(NO_3)_2$ aqueous solution is then added dropwise, and continuously stirred for 1 h at room temperature. 2 mL of 20 mg/mL sodium borohydride aqueous solution is added dropwise under stirring conditions, continuously stirred at room temperature for 1 h, filtered and washed to neutrality, to obtain a nitrogen-doped hierarchical-porous carbon-loaded nano-Pd catalyst.

In contrast to Example 1, the nitrogen-doped hierarchical-porous carbon-loaded nano-Pd catalyst prepared in this example is adjusted in the type of precursor salt, and the type and concentration of the reducing agent in the preparation process. The particle size of the Pd nanoparticles of the prepared catalyst conforms to the normal distribution, and the average particle size is about 5 nm, wherein the content of Pd nanoparticles with a particle size of less than 4 nm accounts for ~40%, which is more than that of Example 1.

Comparative Example 1

1 g of commercially available activated carbon material is weighed, added to 60 mL of deionized water, stirred at room temperature, and slowly added with 1 mL of 100 mg/mL $PdCl_2$ solution, stirred for half an hour and then added with 100 mg/mL of NaOH aqueous solution to adjust the pH value of the mixed solution to 10, and then continuously stirred at room temperature for 1 h. 2 mL of 20 mg/mL formic acid aqueous solution is added dropwise under stirring conditions, continuously stirred at room temperature for 1 h, filtered and washed to neutrality, to obtain an activated carbon-loaded nano-Pd catalyst (referred to as a Pd/AC catalyst).

In contrast to Example 1, the Pd/AC catalyst prepared in this comparative example is prepared by a conventional low-temperature liquid phase reduction method. That is, the addition orders of a Pd salt precursor and lye are exchanged, i.e., the Pd salt precursor is added first, and the pH of the solution is then adjusted.

After testing, the Pd nanoparticles on the Pd/AC catalyst prepared in this comparative example have nonuniform particle sizes, and agglomerate. The Pd nanoparticles have an average particle size of about 5 nm, and are spherical or ellipsoidal, wherein the content of Pd nanoparticles with a particle size of less than 4 nm accounts for 35%, which is more than that of Example 1.

Comparative Example 2

1 g of nitrogen-doped hierarchical-porous carbon material prepared in Example 1 is weighed, added to 60 mL of deionized water, stirred at room temperature, added with 1 mL of 10 mg/mL $PdCl_2$ aqueous solution, stirred for half an hour and then added with 100 mg/mL NaOH aqueous solution dropwise to adjust the pH value of the mixed solution to 10, and continuously stirred at room temperature for 1 h. 2 mL of 20 mg/mL formic acid aqueous solution is added dropwise under stirring conditions, continuously stirred at room temperature for 1 h, filtered and washed to neutrality, to obtain a nitrogen-doped hierarchical-porous carbon-loaded Pd/CN catalyst.

The preparation method of the catalyst in Comparative Example 2 is the same as that in Comparative Example 1, but the nitrogen-doped hierarchical-porous carbon is used as a catalyst carrier. The Pd nano-particles on the prepared Pd/CN catalyst have a uniform particle size. The Pd nanoparticles have an average particle size of about 2 nm, and are spherical or ellipsoidal.

Application Example 1

A selective hydrogenation reaction of catalyzing 6-methyl-5-hepten-2-one (I) is specifically as follows:
  a 50 mL high pressure reaction kettle is used and added with 50 mg of the nitrogen-doped hierarchical-porous carbon-loaded nano-Pd catalyst prepared in Example 1, 15 mmol of 6-methyl-5-hepten-2-one (I) serving as a substrate, and 10 mL of ethanol; 2 MPa of hydrogen is introduced; the reaction temperature is 30° C.; the reaction time is 4 h.

After testing, a conversion rate of 6-methyl-5-hepten-2-one (I) is 100%, and the selectivity of 6-methyl-2-heptanone (II) is 99.9%.

Application Example 2

A selective hydrogenation reaction of catalyzing 6-methyl-5-hepten-2-one (I) is specifically as follows:
  a 50 mL high pressure reaction kettle is used and added with 50 mg of the nitrogen-doped hierarchical-porous carbon-loaded nano-Pd catalyst prepared in Example 2, 15 mmol of 6-methyl-5-hepten-2-one (I) serving as a substrate, and 10 mL of ethanol; 2 MPa of hydrogen is introduced; the reaction temperature is 30° C.; the reaction time is 4 h.

After testing, a conversion rate of 6-methyl-5-hepten-2-one (I) is 100%, and the selectivity of 6-methyl-2-heptanone (II) is 98.9%.

Application Example 3

A selective hydrogenation reaction of catalyzing 6-methyl-5-hepten-2-one (I) is specifically as follows:

a 50 mL high pressure reaction kettle is used and added with 50 mg of the nitrogen-doped hierarchical-porous carbon-loaded nano-Pd catalyst prepared in Example 3, 15 mmol of 6-methyl-5-hepten-2-one (I) serving as a substrate, and 10 mL of ethanol; 2 MPa of hydrogen is introduced; the reaction temperature is 30° C.; the reaction time is 4 h.

After testing, a conversion rate of 6-methyl-5-hepten-2-one (I) is 100%, and the selectivity of 6-methyl-2-heptanone (II) is 96.9%.

Comparative Application Examples 1 to 2

The process conditions are exactly the same as those of Application Example 1, except that the catalysts are respectively replaced with Pd/AC and Pd/CN catalysts prepared in Comparative Example 1 and Comparative Example 2 by the traditional low-temperature reduction method.

After testing, the conversion rate and selectivity of the Pd/AC catalyst are 90% and 72%, respectively, and the conversion rate and selectivity of the Pd/CN catalyst are 95% and 90%, respectively.

It can be seen that the nitrogen-doped hierarchical-porous carbon-loaded nano-Pd catalyst prepared in Example 1 of the present invention is used in the selective hydrogenation reaction of unsaturated ketone, while maintaining the catalyst activity and greatly improving the selectivity.

Application Example 4

The selective hydrogenation reaction of catalyzing 6,10-dimethyl-5-ene-2-undecanone (III) is specifically as follows:
a 50 mL high pressure reaction kettle is used and added with 50 mg of the nitrogen-doped hierarchical-porous carbon-loaded nano-Pd catalyst prepared in Example 1, 15 mmol of 6,10-dimethyl-5-ene-2-undecanone (III) serving as a substrate, and 10 mL of ethanol; 2 MPa of hydrogen is introduced; the reaction temperature is 30° C.; the reaction time is 4 h.

After testing, the conversion rate of 6,10-dimethyl-5-ene-2-undecanone (III) is 100%, and the selectivity of 6,10-dimethyl-2-undecanone (IV) is 99.9%.

Application Example 5

The selective hydrogenation reaction of catalyzing 6,10,14-trimethyl-5-ene-2-pentadecanone (V) is specifically as follows:
a 50 mL high pressure reaction kettle is used and added with 50 mg of the nitrogen-doped hierarchical-porous carbon-loaded nano-Pd catalyst prepared in Example 1, 15 mmol of 6,10,14-trimethyl-5-ene-2-pentadecanone (V) serving as a substrate, and 10 mL of ethanol; 2 MPa of hydrogen is introduced; the reaction temperature is 30° C.; the reaction time is 4 h.

After testing, the conversion rate of 6,10,14-trimethyl-5-ene-2-pentadecanone (V) is 100%, and the selectivity of 6,10,14-trimethyl-2-pentadecanone (VI) is 99.8%.

Application Example 6

The selective hydrogenation reaction of catalyzing 6-methyl-3,5-heptadiene-2-one (VII) is specifically as follows:
a 50 mL high pressure reaction kettle is used and added with 50 mg of the nitrogen-doped hierarchical-porous carbon-loaded nano-Pd catalyst prepared in Example 1, 15 mmol of 6-methyl-3,5-heptadiene-2-one (VII) serving as a substrate, and 10 mL of ethanol; 2 MPa of hydrogen is introduced; the reaction temperature is 30° C.; the reaction time is 4 h.

After testing, the conversion rate of 6-methyl-3,5-heptadiene-2-one (VII) is 100%, and the selectivity of 6-methyl-2-heptanone (II) is 99.8%.

Application Example 7

The selective hydrogenation reaction of catalyzing 6,10-dimethyl-5,9-diene-2-undecanone (VIII) is specifically as follows:
a 50 mL high pressure reaction kettle is used and added with 50 mg of the nitrogen-doped hierarchical-porous carbon-loaded nano-Pd catalyst prepared in Example 1, 15 mmol of 6,10-dimethyl-5,9-diene-2-undecanone (VIII) serving as a substrate, and 10 mL of ethanol; 2 MPa of hydrogen is introduced; the reaction temperature is 30° C.; the reaction time is 4 h.

After testing, the conversion rate of 6,10-dimethyl-5,9-diene-2-undecanone (VIII) is 100%, and the selectivity of 6,10-dimethy-2-undecanone (IV) is 99.8%.

Application Example 8

The selective hydrogenation reaction of catalyzing 6,10-dimethyl-3,5-diene-2-undecanone (IX) is specifically as follows:
a 50 mL high pressure reaction kettle is used and added with 50 mg of the nitrogen-doped hierarchical-porous carbon-loaded nano-Pd catalyst prepared in Example 1, 15 mmol of 6,10-dimethyl-3,5-diene-2-undecanone (IX) serving as a substrate, and 10 mL of ethanol; 2 MPa of hydrogen is introduced; the reaction temperature is 30° C.; the reaction time is 4 h.

After testing, the conversion rate of 6,10-dimethyl-3,5-diene-2-undecanone (IX) is 100%, and the selectivity of 6,10-dimethy-2-undecanone (IV) is 99.9%.

Application Example 9

The selective hydrogenation reaction of catalyzing 6,10,14-trimethyl-3,5-diene-2-pentadecanone (X) is specifically as follows:
a 50 mL high pressure reaction kettle is used and added with 50 mg of the nitrogen-doped hierarchical-porous carbon-loaded nano-Pd catalyst prepared in Example 1, 15 mmol of 6,10,14-trimethyl-3,5-diene-2-pentadecanone (X) serving as a substrate, and 10 mL of ethanol; 2 MPa of hydrogen is introduced; the reaction temperature is 30° C.; the reaction time is 4 h.

After testing, the conversion rate of 6,10,14-trimethyl-3,5-diene-2-pentadecanone (X) is 100%, and the selectivity of 6,10,14-trimethyl-2-pentadecanone (VI) is 99.9%.

Application Example 10

The selective hydrogenation reaction of catalyzing 6,10,14-trimethyl-5,9,13-triene-2-pentadecanone (XI) is specifically as follows:
a 50 mL high pressure reaction kettle is used and added with 50 mg of the nitrogen-doped hierarchical-porous carbon-loaded nano-Pd catalyst prepared in Example 1, 15 mmol of 6,10,14-trimethyl-5,9,13-triene-2-pentadecanone (XI) serving as a substrate, and 10 mL of ethanol; 2 MPa of hydrogen is introduced; the reaction temperature is 30° C.; the reaction time is 4 h.

After testing, the conversion rate of 6,10,14-trimethyl-5,9,13-triene-2-pentadecanone (XI) is 100%, and the selectivity of 6,10,14-trimethyl-2-pentadecanone (VI) is 99.8%.

Application Example 11

The selective hydrogenation reaction of catalyzing cis-3,7-dimethyl-2,6-diene-octanal (XII) is specifically as follows:
a 50 mL high pressure reaction kettle is used and added with 50 mg of the nitrogen-doped hierarchical-porous carbon-loaded nano-Pd catalyst prepared in Example 1, 15 mmol of cis-3,7-dimethyl-2,6-diene-octanal (XII) serving as a substrate, and 10 mL of ethanol; 2 MPa of hydrogen is introduced; the reaction temperature is 30° C.; the reaction time is 4 h.

After testing, the conversion rate of the cis-3,7-dimethyl-2,6-diene-octanal (XII) is 100%, and the selectivity of the 3,7-dimethyl-octanal (XIII) is 99.6%.

Application Example 12

The selective hydrogenation reaction of catalyzing trans-3,7-dimethyl-2,6-diene-octanal (XIV) is specifically as follows:
a 50 mL high pressure reaction kettle is used and added with 50 mg of the nitrogen-doped hierarchical-porous carbon-loaded nano-Pd catalyst prepared in Example 1, 15 mmol of trans-3,7-dimethyl-2,6-diene-octanal (XIV) serving as a substrate, and 10 mL of ethanol; 2 MPa of hydrogen is introduced; the reaction temperature is 30° C.; the reaction time is 4 h.

After testing, the conversion rate of the trans-3,7-dimethyl-2,6-diene-octanal (XIV) is 100%, and the selectivity of the 3,7-dimethyl-octanal (XIII) is 99.8%.

Application Example 13

The comparison of mechanical application performances of the selective hydrogenation reaction of catalyzing 6-methyl-3,5-heptadiene-2-one (VII) is specifically as follows:
a double-kettle parallel experiment is adopted in the mechanical application of each catalyst. A 50 mL high pressure reaction kettle is used and respectively added with the nitrogen-doped hierarchical-porous carbon-loaded nano-Pd catalyst in Example 1, 50 mg of the catalysts prepared in Comparative Example 1 and Comparative Example 2, 15 mmol of 6-methyl-3,5-heptadiene-2-one (VII) and 10 mL of ethanol; 2 MPa of hydrogen is introduced; the reaction temperature is 30° C.; the reaction time is 4 h. After the reaction, the catalysts in the two kettles are taken out by centrifugation, washed with ethanol for 3 times, and dried in vacuum at 40° C. The catalyst in one of the kettles is supplemented with the catalyst in the parallel experiment kettle and then continues to be used for the selective hydrogenation reaction of the 6-methyl-3,5-heptadiene-2-one (VII).

Figure 7:
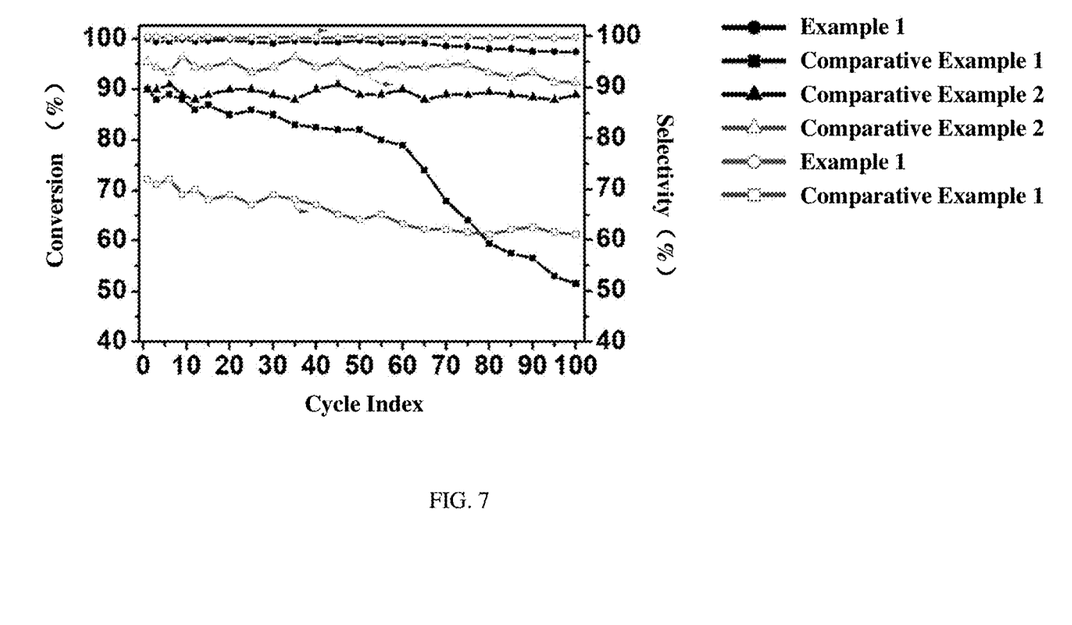
FIG. 7 shows cyclic application performance comparison curves of the preparation of 6-methyl-2-heptanone (II) by the selective hydrogenation of 6-methyl-3,5-heptadiene-2-one (VII) in the catalysts prepared in Example 1, Comparative Example 1 and Comparative Example 2.

The results of the mechanical application are shown in FIG. 7. It can be found that the performances of the nitrogen-doped hierarchical-porous carbon-loaded nano-Pd catalyst of Example 1 are stable, and the activity and selectivity can still be maintained after 100 times of mechanical application. The activity and selectivity of the Pd/AC catalyst prepared in Comparative Example 1 decrease significantly with the increase in the number of mechanical applications. After 100 times of mechanical applications, the conversion rate and selectivity could only be maintained at about 50% and 60%, respectively. The conversion rate and selectivity of the Pd/CN catalyst prepared in Comparative Example 2 are maintained at initial values of approximately 90% and 95%.

Application Example 14

The comparison of mechanical application performances of catalyzing the selective hydrogenation reaction of 6,10-dimethyl-3,5-diene-2-undecanone (IX) is specifically as follows:
a double-kettle parallel experiment is adopted in the mechanical application of a catalyst. a 50 mL high pressure reaction kettle is used and added with 50 mg of the nitrogen-doped hierarchical-porous carbon-loaded nano-Pd catalyst prepared in Example 1, 15 mmol of 6,10-dimethyl-3,5-diene-2-undecanone (IX) and 10 mL of ethanol; 2 MPa of hydrogen is introduced; the reaction temperature is 30° C.; the reaction time is 4 h. After the reaction, the catalysts in the two kettles are taken out by centrifugation, washed with ethanol 3 for times, and dried in vacuum at 40° C. The catalyst in one of the kettles is supplemented with the catalyst in the parallel experiment kettle and continues to be used for the selective hydrogenation reaction of the 6,10-dimethyl-3,5-diene-2-undecanone (IX).

Figure 8:
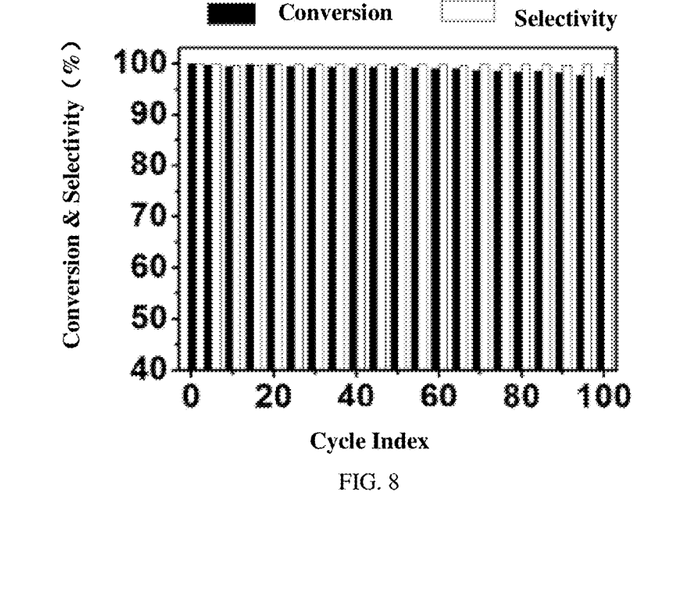
FIG. 8 shows a cyclic application performance comparison curve of the preparation of 6,10-dimethyl-2-undecanone (IV) by the selective hydrogenation of 6,10-dimethyl-3,5-diene-2-undecanone (IX) in the catalyst prepared in Example 1.

The results of the mechanical application are shown in FIG. 8. It can be found that the performances of the nitrogen-doped hierarchical-porous carbon-loaded nano-Pd catalyst of Example 1 are stable, and the selectivity can still be maintained after 100 times of mechanical application, with only a slight decrease in activity.

Application Example 15

The comparison of mechanical application performances of catalyzing the selective hydrogenation reaction of 6,10,14-trimethyl-3,5-diene-2-pentadecanone (X) is specifically as follows:
a double-kettle parallel experiment is adopted in the mechanical application of a catalyst. a 50 mL high pressure reaction kettle is used and added with 50 mg of the nitrogen-doped hierarchical-porous carbon-loaded nano-Pd catalyst prepared in Example 1, 15 mmol of 6,10,14-trimethyl-3,5-diene-2-pentadecanone (X) and 10 mL of ethanol; 2 MPa of hydrogen is introduced; the reaction temperature is 30° C.; the reaction time is 4 h. After the reaction, the catalysts in the two kettles are taken out by centrifugation, washed with ethanol for 3 times, and dried in vacuum at 40° C. The catalyst in one of the kettles is supplemented with the catalyst in the parallel experiment kettle and continues to be used for the selective hydrogenation reaction of the 6,10,14-Trimethyl-3,5-diene-2-pentadecanone (X).

Figure 9:
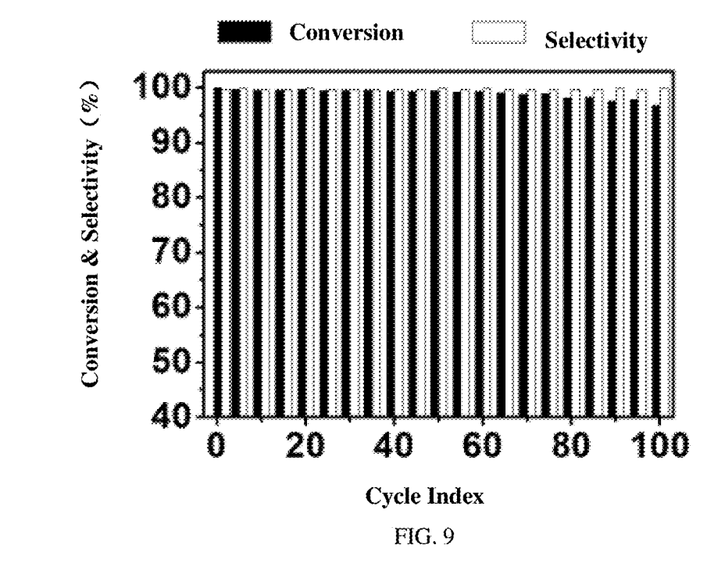
FIG. 9 shows a cyclic application performance comparison curve of the preparation of 6,10,14-trimethyl-2-pentadecanone (VI) by the selective hydrogenation of 6,10,14-trimethyl-3,5-diene-2-pentadecanone (X) in the catalyst prepared in Example 1.

The results of the mechanical application are shown in FIG. 9. It can be found that the performances of the nitrogen-doped hierarchical-porous carbon-loaded nano-Pd catalyst of Example 1 are stable, and the selectivity can still be maintained after 100 times of mechanical application, with only a slight decrease in activity.

The technical features of the above-described examples may be arbitrarily combined. For the sake of brevity of description, all possible combinations of the technical features in the above examples are not described. However, as long as there is no contradiction between the combinations of these technical features, they should be considered as the scope of the description.

The above-described examples are merely illustrative of several embodiments of the present invention, and the description thereof is more specific and detailed, but is not to be construed as limiting the scope of the present invention. It should be noted that a number of variations and modifications may be made by those of ordinary skill in the art without departing from the concept of the present invention, all fall within the protection scope of the present invention. Therefore, the protection scope of the present invention should be determined by the appended claims.

The invention claimed is:

1. A preparation method of a nitrogen-doped hierarchical-porous carbon-loaded nano-Pd catalyst, comprising:
   1) Preparing nitrogen-doped hierarchical-porous carbon;
   2) Mixing the nitrogen-doped hierarchical-porous carbon prepared in step 1) with water, and adjusting a pH value of the mixed solution to be alkaline; and
   3) Mixing the mixed solution prepared in step 2) with a Pd metal precursor aqueous solution, and then adding a reducing agent to obtain the nitrogen-doped hierarchical-porous carbon-loaded nano-Pd catalyst after reduction.

2. The preparation method of the nitrogen-doped hierarchical-porous carbon-loaded nano-Pd catalyst according to claim 1, wherein in step 2):
   a mass-volume ratio of the nitrogen-doped hierarchical-porous carbon to water is 1:20-200 g/mL; and
   the pH value of the mixed solution is adjusted to 8-12.

3. A nitrogen-doped hierarchical-porous carbon-loaded nano-Pd catalyst formed according to the method of claim 2, comprising:
   a nitrogen-doped porous carbon material carrier with hierarchical pores, and
   Pd metal nanoparticles loaded in the hierarchical pores of the carrier, wherein:
      the Pd metal nanoparticles have a particle size of 2-14 nm, and are each of a regular polyhedron shape; and
      the mass fraction of the Pd metal nanoparticles is 0.1%-10%.

4. A method of performing a catalytic hydrogenation reaction, comprising:
   providing the nitrogen-doped hierarchical-porous carbon-loaded nano-Pd catalyst according to claim 3;
   providing a substrate for the nitrogen-doped hierarchical-porous carbon-loaded nano-Pd catalyst; and
   performing a catalytic hydrogenation reaction on the substrate with the nitrogen-doped hierarchical-porous carbon loaded nano-Pd catalyst.

5. The method according to claim 4, wherein:
   the substrate is an unsaturated ketone; and
   the unsaturated ketone is at least one selected from the group consisting of 6-methyl-5-heptene-2-one, 6-methyl-3,5-heptadiene-2-one, 6,10-dimethyl-5-ene-2-undecanone, 6,10-dimethyl-5,9-diene-2-undecanone, 6,10-dimethyl-3,5-diene-2-undecanone, 6,10,14-trimethyl-5-ene-2-pentadecanone, 6,10,14-trimethyl-5,9,13-triene-2-pentadecanone, 6,10,14-trimethyl-3,5-diene-2-pentadecanone, cis-3,7-dimethyl-2,6-diene-octanal, and trans-3,7-dimethyl-2,6-diene-octanal.

6. The preparation method of the nitrogen-doped hierarchical-porous carbon-loaded nano-Pd catalyst according to claim 1, wherein in step 3):
   the Pd metal precursor is selected from soluble salts of Pd metal;
   the concentration of the Pd metal precursor aqueous solution is 1-50 mg/mL; and
   a mass ratio of the nitrogen-doped hierarchical-porous carbon to the Pd metal precursor is (3-600):1.

7. A nitrogen-doped hierarchical-porous carbon-loaded nano-Pd catalyst formed according to the method of claim 6, comprising:
   a nitrogen-doped porous carbon material carrier with hierarchical pores, and
   Pd metal nanoparticles loaded in the hierarchical pores of the carrier, wherein:
      the Pd metal nanoparticles have a particle size of 2-14 nm, and are each of a regular polyhedron shape; and
      the mass fraction of the Pd metal nanoparticles is 0.1%-10%.

8. A method of performing a catalytic hydrogenation reaction, comprising:
   providing the nitrogen-doped hierarchical-porous carbon-loaded nano-Pd catalyst according to claim 7;
   providing a substrate for the nitrogen-doped hierarchical-porous carbon-loaded nano-Pd catalyst; and
   performing a catalytic hydrogenation reaction on the substrate with the nitrogen-doped hierarchical-porous carbon loaded nano-Pd catalyst.

9. The method according to claim 8, wherein:
   the substrate is an unsaturated ketone; and
   the unsaturated ketone is at least one selected from the group consisting of 6-methyl-5-heptene-2-one, 6-methyl-3,5-heptadiene-2-one, 6,10-dimethyl-5-ene-2-undecanone, 6,10-dimethyl-5,9-diene-2-undecanone, 6,10-dimethyl-3,5-diene-2-undecanone, 6,10,14-trimethyl-5-ene-2-pentadecanone, 6,10,14-trimethyl-5,9,13-triene-2-pentadecanone, 6,10,14-trimethyl-3,5-diene-2-pentadecanone, cis-3,7-dimethyl-2,6-diene-octanal, and trans-3,7-dimethyl-2,6-diene-octanal.

10. The preparation method of the nitrogen-doped hierarchical-porous carbon-loaded nano-Pd catalyst according to claim 1, wherein in step 3):
   the reducing agent is selected from at least one of hydrazine hydrate, formic acid, sodium borohydride, and sodium formate; and
   a mass ratio of the reducing agent to the Pd metal precursor is (1-20):1.

11. The preparation method of the nitrogen-doped hierarchical-porous carbon-loaded nano-Pd catalyst according to claim 10, wherein the reducing agent is added in a form of a reducing agent aqueous solution, and a mass-volume ratio of the reducing agent to water is 1-20 mg/mL.

12. A nitrogen-doped hierarchical-porous carbon-loaded nano-Pd catalyst formed according to the method of claim 11, comprising:
   a nitrogen-doped porous carbon material carrier with hierarchical pores, and
   Pd metal nanoparticles loaded in the hierarchical pores of the carrier, wherein:
      the Pd metal nanoparticles have a particle size of 2-14 nm, and are each of a regular polyhedron shape; and
      the mass fraction of the Pd metal nanoparticles is 0.1%-10%.

13. A nitrogen-doped hierarchical-porous carbon-loaded nano-Pd catalyst formed according to the method of claim 10, comprising:
   a nitrogen-doped porous carbon material carrier with hierarchical pores, and Pd metal nanoparticles loaded in the hierarchical pores of the carrier, wherein:
- the Pd metal nanoparticles have a particle size of 2-14 nm, and are each of a regular polyhedron shape; and
- the mass fraction of the Pd metal nanoparticles is 0.1%-10%.

14. The preparation method of the nitrogen-doped hierarchical-porous carbon-loaded nano-Pd catalyst according to claim 1, wherein in step 3):
the reduction temperature is 0-80° C., and the reduction time is 1-360 min.

15. A nitrogen-doped hierarchical-porous carbon-loaded nano-Pd catalyst formed according to the method of claim 14, comprising:
a nitrogen-doped porous carbon material carrier with hierarchical pores, and
Pd metal nanoparticles loaded in the hierarchical pores of the carrier, wherein:
- the Pd metal nanoparticles have a particle size of 2-14 nm, and are each of a regular polyhedron shape; and
- the mass fraction of the Pd metal nanoparticles is 0.1%-10%.

16. The preparation method of the nitrogen-doped hierarchical-porous carbon-loaded nano-Pd catalyst according to claim 1, wherein in step 3):
- the reduced product is filtered to obtain the nitrogen-doped hierarchical-porous carbon-loaded nano-Pd catalyst; and
- the water content of the nitrogen-doped hierarchical-porous carbon-loaded nano-Pd catalyst is 5-75 wt %.

17. A nitrogen-doped hierarchical-porous carbon-loaded nano-Pd catalyst formed according to the method of claim 16, comprising:
a nitrogen-doped porous carbon material carrier with hierarchical pores, and
Pd metal nanoparticles loaded in the hierarchical pores of the carrier, wherein:
- the Pd metal nanoparticles have a particle size of 2-14 nm, and are each of a regular polyhedron shape; and
- the mass fraction of the Pd metal nanoparticles is 0.1%-10%.

18. A nitrogen-doped hierarchical-porous carbon-loaded nano-Pd catalyst formed according to the method of claim 1, comprising:
a nitrogen-doped porous carbon material carrier with hierarchical pores, and
Pd metal nanoparticles loaded in the hierarchical pores of the carrier, wherein:
- the Pd metal nanoparticles have a particle size of 2-14 nm, and are each of a regular polyhedron shape; and
- the mass fraction of the Pd metal nanoparticles is 0.1%-10%.

19. A method of performing a catalytic hydrogenation reaction, comprising:
- providing of the nitrogen-doped hierarchical-porous carbon-loaded nano-Pd catalyst according to claim 18;
- providing a substrate for the nitrogen-doped hierarchical-porous carbon loaded nano-Pd catalyst; and
- performing a catalytic hydrogenation reaction on the substrate with the nitrogen-doped hierarchical-porous carbon loaded nano-Pd catalyst.

20. The method according to claim 19, wherein:
the substrate is an unsaturated ketone; and
the unsaturated ketone is at least one selected from the group consisting at least one of 6-methyl-5-heptene-2-one, 6-methyl-3,5-heptadiene-2-one, 6,10-dimethyl-5-ene-2-undecanone, 6,10-dimethyl-5,9-diene-2-undecanone, 6,10-dimethyl-3,5-diene-2-undecanone, 6,10,14-trimethyl-5-ene-2-pentadecanone, 6,10,14-trimethyl-5,9,13-triene-2-pentadecanone, 6,10,14-trimethyl-3,5-diene-2-pentadecanone, cis-3,7-dimethyl-2,6-diene-octanal, and trans-3,7-dimethyl-2,6-diene-octanal.

\* \* \* \* \*